United States Patent
Webb et al.

(10) Patent No.: US 6,211,195 B1
(45) Date of Patent: Apr. 3, 2001

(54) CRF ANTAGONISTIC THIOPHENOPYRIDINES

(75) Inventors: Thomas R. Webb, Olivenhain; James R. McCarthy, San Diego, both of CA (US)

(73) Assignees: Neurocrine Biosciences, Inc., San Diego, CA (US); Janssen Pharmaceutica N.V., Beerse (BE)

(*) Notice: Subject to any disclaimer, the term of this patent is extended or adjusted under 35 U.S.C. 154(b) by 0 days.

(21) Appl. No.: 09/403,400

(22) PCT Filed: Apr. 15, 1998

(86) PCT No.: PCT/EP98/02268

§ 371 Date: Oct. 19, 1999

§ 102(e) Date: Oct. 19, 1999

(87) PCT Pub. No.: WO98/47903

PCT Pub. Date: Oct. 29, 1998

Related U.S. Application Data

(60) Provisional application No. 60/044,524, filed on Apr. 22, 1997.

(51) Int. Cl.$^7$ .................................................... A01N 43/42
(52) U.S. Cl. ..................... 514/301; 514/211; 514/233.8; 540/597; 544/127; 546/114
(58) Field of Search ................. 546/114; 514/301, 514/233.8, 211; 544/127; 540/597

(56) References Cited

FOREIGN PATENT DOCUMENTS

WO 96/35689    11/1996   (WO).
WO 98/08847     5/1998   (WO).

OTHER PUBLICATIONS

Patterson et al, The Ring Index, 2nd Ed., p. 175, 1960.*

* cited by examiner

*Primary Examiner*—Bernard Dentz
(74) *Attorney, Agent, or Firm*—Scully, Scott, Murphy & Presser

(57) ABSTRACT

This invention concerns compounds of formula

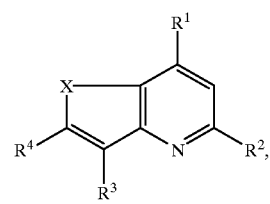

(I)

including the stereoisomers and the pharmaceutically acceptable acid addition salt forms thereof, wherein X is S or $SO_2$; $R^1$ is $C_{1-6}$alkyl, $NR^5R^6$, $OR^6$ or $SR^6$; $R^2$ is $C_{1-6}$alkyl, $C_{1-6}$alkyloxy or $C_{1-6}$alkylthio; $R^3$ is $Ar^1$ or $Het^1$; $R^4$ is hydrogen, $C_{1-6}$alkyl, $C_{1-6}$alkylsulfonyl, $C_{1-6}$alkylsulfoxy or $C_{1-6}$alkylthio; $R^5$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl; $R^6$ is $C_{1-8}$alkyl, mono- or di($C_{3-6}$cycloalkyl)methyl, $Ar^2CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl)amino$C_{1-6}$alkyl, di($C_{1-6}$alkyl)amino, $C_{1-6}$alkylcarbonyl$C_{1-6}$alkyl; or $R^5$ and $R^6$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl; and $Ar^1$ and $Ar^2$ are each optionally substituted phenyl; and $Het^1$ is optionally substituted pyridinyl; having CRF receptor antagonistic properties; pharmaceutical compositions containing such compounds as active ingredients; methods of treating disorders related to hypersecretion of CRF such as depression, anxiety, substance abuse, by administering an effective amount of a compound of formula (I).

16 Claims, No Drawings

CRF ANTAGONISTIC THIOPHENOPYRIDINES

This application claim benefit to Provisional application 60/044,524 filed Apr. 22, 1997.

BACKGROUND OF THE INVENTION

This invention relates to thiophenopyridines which possess CRF receptor antagonistic properties, to pharmaceutical compositions containing these compounds as active ingredient, and the use thereof in the treatment of endocrine, psychiatric and neurologic conditions or illnesses, including stress-related disorders in general.

The first corticotropin-releasing factor (CRF) was isolated from ovine hypothalmi and identified as a 41-amino acid peptide (Vale et al., Science 213:1394–1397, 1981). Subsequently, sequences of human and rat CRF were isolated and determined to be identical, but different from ovine CRF in 7 of the 41 amino acid residues (Rivier et al., Proc. Natl. Acad. Sci. USA 80:4851, 1983; Shibahara et al., EMBO J. 2:775, 1983). CRF has been found to produce profound alterations in endocrine, nervous and immune system function. CRF is believed to be the major physiological regulator of the basal and stress-release of adrenocorticotropic hormone ("ACTH"), β-endorphin, and other pro-opiomelanocortin ("POMC")-derived peptides from the anterior pituitary (Vale et al., Science 213:1394–1397, 1981). Briefly, CRF is believed to initiate its biological effects by binding to a plasma membrane receptor which has been found to be distributed throughout the brain (DeSouza et al., Science 221:1449–1451, 1984), pituitary (DeSouza et al., Methods Enzymol. 124:560, 1986; Wynn et al., Biochem. Biophys. Res. Comm. 110:602–608, 1983), adrenals (Udelsman et al., Nature 319:147–150, 1986) and spleen (Webster, E. L., and E. B. DeSouza, Endocrinology 122:609–617, 1988). The CRF receptor is coupled to a GTP-binding protein (Perrin et al., Endocrinology 118:1171–1179, 1986) which mediates CRF-stimulated increase in intracellular production of cAMP (Bilezikjian, L. M., and W. W. Vale, Endocrinology 113:657–662, 1983).

In addition to its role in stimulating the production of ACTH and POMC, CRF is also believed to coordinate many of the endocrine autonomic, and behavioral responses to stress, and may be involved in the pathophysiology of affective disorders. Moreover, CRF is believed to be a key intermediary in communication between the imnune, central nervous, endocrine and cardiovascular systems (Crofford et al., J. Clin. Invest. 90:2555–2564, 1992; Sapolsky et al., Science 238:522–524, 1987; Tilders et al., Regul. Peptides 5:77–84, 1982). Overall, CRF appears to be one of the pivotal central nervous system neurotransmitters and plays a crucial role in integrating the body's overall response to stress.

Administration of CRF directly to the brain elicits behavioral, physiological, and endocrine responses identical to those observed for an animal exposed to a stressful environment. For example, intracerebroventricular injection of CRF results in behavioral activation (Sutton et al., Nature 297:331, 1982), persistent activation of the electroencephalogram (Ehlers et al., Brain Res. 2/8332, 1983), stimulation of the sympathoadrenomedullary pathway (Brown et al., Endocrinology 110:928, 1982), an increase of heart rate and blood pressure (Fisher et al., Endocrinology 110:2222, 1982), an increase in oxygen consumption (Brown et al., Life Sciences 30:207, 1982), alteration of gastrointestinal activity (Williams et al., Am. J. Physiol. 253:G582, 1987), suppression of food consumption (Levine et al., Neuropharmacology 22:337, 1983), modification of sexual behavior (Sirinathsinghji et al., Nature 305:232, 1983), and immune function compromise (Irwin et al., Am. J. Physiol. 255:R744, 1988). Furthermore, clinical data suggest that CRF may be hypersecreted in the brain in depression, anxiety-related disorders, and anorexia nervosa. (DeSouza, Ann. Reports in Med. Chem. 25:215–223, 1990).

Accordingly, clinical data suggest that CRF receptor antagonists may represent novel antidepressant and/or anxiolytic drugs that may be usefull in the treatment of the neuropsychiatric disorders manifesting hypersecretion of CRF.

Due to the physiological significance of CRF, the development of further biologically active small molecules having significant CRF receptor binding activity and which are capable of antagonizing the CRF receptor remains a desirable goal. Such CRF receptor antagonists would be useful in the treatment of endocrine, psychiatric and neurologic conditions or illnesses, including stress-related disorders in general.

CRF receptor antagonists have been reported in for example, WO-94/13676, WO-94/13677 and WO-95/33750 which disclose pyrrolopyrimidines, pyrazolo[3,4-d] pyrimidines and substituted purines as CRF receptor antagonists. EP-0,452,002 discloses thienopyrimidines having fungicidal, insecticidal and miticidal utility. Further, EP-0,209,977 discloses thienopyridones as antihypertensive agents.

The compounds of the present invention differ from the cited art-known compounds structurally, by the nature of the substituents on the thiophenopyridine moiety, and pharmacologically by the fact that, unexpectedly, these compounds have CRF antagonistic properties.

DESCRIPTION OF THE INVENTION

This invention concerns compounds of formula (I)

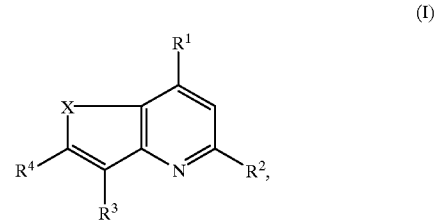

including the stereoisomers and the phanmaceutically acceptable acid addition salt forms thereof, wherein
X is S or $SO_2$;
$R^1$ is $C_{1-6}$alkyl; $NR^5R^6$, $OR^6$ or $SR^6$;
$R^2$ is $C_{1-6}$alkyl, $C_{1-6}$alkyloxy or $C_{1-6}$alkylthio;
$R^3$ is $Ar^1$ or $Het^1$;
$R^4$ is hydrogen or $C_{1-6}$alkyl;
$R^5$ is hydrogen, $C_{1-8}$alkyl, mono- or di($C_{3-6}$cycloalkyl) methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl;
$R^6$ is $C_{1-8}$alkyl, mono- or di($C_{3-6}$cycloalkyl)methyl, $Ar^2CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl)amino$C_{1-6}$alkyl, di($C_{1-6}$alkyl)amino, $C_{1-6}$alkylcarbonyl$C_{1-6}$alkyl;
or $R^5$ and $R^6$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl; and Ar$^1$ is phenyl; phenyl substituted with 1, 2 or 3 substituents each independently selected from halo, C$_{1-6}$alkyl, trifluoromethyl, hydroxy, cyano, C$_{1-6}$alkyloxy, benzyloxy, C$_{1-6}$alkylthio, nitro, amino and mono- or di(C$_{1-6}$alkyl)amino;

Het$^1$ is pyridinyl; pyridinyl substituted with 1, 2 or 3 substituents each independently selected from halo, C$_{1-6}$alkyl, trifluoromethyl, hydroxy, cyano, C$_{1-6}$alkyloxy, benzyloxy, C$_{1-6}$alkylthio, nitro, amino, and mono- or di(C$_{1-6}$alkyl)amino; and Ar$^2$ is phenyl; phenyl substituted with 1, 2 or 3 substituents each independently selected from halo, C$_{1-6}$alkyl, C$_{1-6}$alkyloxy, di(C$_{1-6}$alkyl)aminoC$_{1-6}$alkyl, or trifluoromethyl.

As used in the foregoing definitions and hereinafter, halo is generic to fluoro, chloro, bromo and iodo; C$_{1-2}$alkyl defines straight saturated hydrocarbon radicals having from 1 to 2 carbon atoms such as methyl and ethyl; C$_{2-4}$alkyl defines straight and branched chain saturated hydrocarbon radicals having from 2 to 4 carbon atoms such as ethyl, propyl, butyl, 1-methylethyl and the like; C$_{3-4}$alkyl defines straight and branched chain saturated hydrocarbon radicals having from 3 to 4 carbon atoms such as propyl, butyl, 1-methylethyl and the like; C$_{1-6}$alkyl includes C$_{1-2}$alkyl and C$_{3-4}$alkyl radicals as defined hereinbefore and the higher homologues thereof having from 5 to 6 carbon atoms such as, pentyl, the pentyl isomers, hexyl and the hexyl isomers; C$_{1-8}$alkyl includes C$_{1-6}$alkyl and the higher homologues thereof having from 7 to 8 carbon atoms such as, for example, heptyl, octyl and the like; C$_{3-6}$alkenyl defines straight and branched chain hydrocarbon radicals containing one double bond and having from 3 to 6 carbon atoms such as, for example, 2-propenyl, 3-butenyl, 2-pentenyl, 3-pentenyl, 3-methyl-2-butenyl, and the like; and where said C$_{3-6}$alkenyl is linked to a nitrogen or oxygen, the carbon atom making the link preferably is saturated. C$_{3-6}$cycloalkyl comprises cyclopropyl, cyclobutyl, cyclopentyl and cyclohexyl. HydroxyC$_{1-6}$alkyl refers to C$_{1-6}$alkyl substituted with a hydroxy group.

Depending on the nature of some of the substituents, the compounds of formula (I) may contain one or more asymmetric centers which may be designated with the generally used R and S nomenclature.

The pharmaceutically acceptable acid addition salts as mentioned hereinabove are meant to comprise the therapeutically active non-toxic acid addition salt forms which the compounds of formula (I) are able to form. The compounds of formula (I) which have basic properties can be converted in their pharmaceutically acceptable acid addition salts by treating said base form with an appropriate acid. Appropriate acids comprise, for example, inorganic acids such as hydrohalic acids, e.g. hydrochloric or hydrobromic acid; sulfuric; nitric; phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-amino-salicylic, pamoic and the like acids.

The term acid addition salts also comprises the hydrates and the solvent addition forms which the compounds of formula (I) are able to form. Examples of such forms are e.g. hydrates, alcoholates and the like.

The term stereochemically isomeric forms of compounds of formula (I), as used hereinbefore, defines all possible compounds made up of the same atoms bonded by the same sequence of bonds but having different three-dimensional structures which are not interchangeable, which the compounds of formula (I) may possess. Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of formula (I) both in pure form or in admixture with each other are intended to be embraced within the scope of the present invention.

Some of the compounds of formula (I) may also exist in their tautomeric forms. Such forms although not explicitly indicated in the above formula are intended to be included within the scope of the present invention. For instance, compounds of formula (I) wherein Het$^1$ is pyridinyl substituted with hydroxy, may exist in their corresponding tautomeric form.

Whenever used hereinafter, the term "compounds of formula (I)" is meant to include also the pharmaceutically acceptable acid addition salts and all stereoisomeric forms.

Particular groups of compounds within the invention are those compounds of formula (I) wherein one or more of the following restrictions apply:

a) X is S or SO$_2$; in particular X is S;
b) R$^1$ is NR$^5$R$^6$ wherein R$^5$ is C$_{1-8}$alkyl or C$_{1-6}$alkyloxyC$_{1-6}$alkyl; in particular C$_{2-4}$alkyl or C$_{1-2}$alkyloxyC$_{2-4}$alkyl; and R$^6$ is C$_{1-8}$alkyl, C$_{1-6}$alkyloxyC$_{1-6}$alkyl, Ar$^2$CH$_2$ or C$_{3-6}$cycloalkylmethyl; in particular C$_{2-4}$alkyl, C$_{1-2}$alkyloxyC$_{2-4}$alkyl, phenylmethyl or cyclopropylmethyl;
c) R$^2$ is C$_{1-6}$alkyl; in particular C$_{1-2}$alkyl;
d) R$^3$ is a phenyl substituted with 1, 2 or 3 substituents each independently selected from C$_{1-6}$alkyl, C$_{1-6}$alkyloxy or halo; wherein the phenyl moiety is preferably substituted in the 3-, 4-, 6-, 2,4- or 2,4,6-positions; or R$^3$ is a pyridinyl substituted with 1, 2 or 3 substituents each independently selected from halo, amino, nitro, trifluoromethyl, mono- or di(C$_{1-6}$alkyl)amino, piperidinyl or C$_{1-6}$alkyl; wherein the pyridinyl moiety preferably is connected via the 2- or 3-position to the remainder of the molecule;
e) R$^4$ is hydrogen or C$_{1-6}$alkyl; in particular R$^4$ is hydrogen or C$_{1-2}$alkyl.

Preferred compounds are those compounds of formula (I) wherein R$^1$ is NR$^5$R$^6$ and R$^5$ is C$_{3-4}$alkyl, preferably propyl; R$^6$ is C$_{3-4}$alkyl, phenylmethyl or cyclopropylmethyl, preferably propyl or phenylmethyl; R$^2$ is methyl; R$^3$ is a phenyl substituted with 1, 2 or 3 substituents each independently selected from halo, methyl or methoxy; or R$^3$ is pyridinyl substituted with 1, 2 or 3 substituents each independently selected from halo, methyl or dimethylamino; and R$^4$ is hydrogen.

Most preferred are those compounds selected from 7-(dipropylamino)-5-methyl-3-(2',4',6'-trimethylphenyl)thieno(3,2-b)pyridine; and 7-(N-benzyl-N-propylamino)-5-methyl-3-(2',4',6'-trimethylphenyl)thieno(3,2-b)-pyridine; the stereoisomeric forms and the pharmaceutically acceptable acid addition salts thereof.

Compounds of formula (I-a), defined as compounds of formula (I) wherein R$^{1'}$ has the meaning of R$^1$ other than C$_{1-6}$alkyl, can be prepared by reacting an intermediate of formula (II) with an intermediate of formula (III). In intermediate (II), W is an appropriate leaving group such as halo, e.g. chloro, bromo, or a sulfonyloxy group, e.g. a mesyloxy or a tosyloxy group.

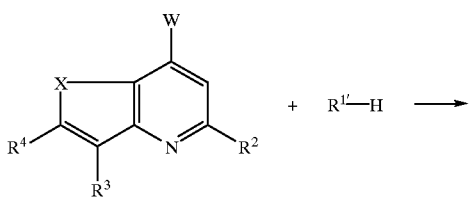

(II)  (III)

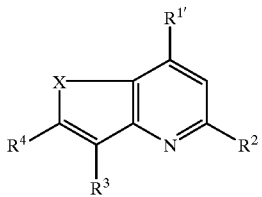

(I-a)

Said reaction can be performed in a reaction-inert solvent such as, for example, acetonitrile, N,N-dimethylformamide, methyl isobutylketone, tetrahydrofuran or dichloromethane; and in the presence of a suitable base such as, for example, sodium carbonate, sodium hydrogen carbonate or triethylamine. When the intermediates of formula (III) are volatile amines, said reaction may also be performed in a sealed reaction vial. Stirring may enhance the rate of the reaction. The reaction may conveniently be carried out at a temperature ranging between room temperature and reflux temperature, and optionally is the presence of a suitable catalyst.

Also, compounds of formula (I) wherein $R^1$ is $OR^6$, said compounds being represented by formula (I-b), may be prepared by O-alkylating an intermediate of formula (IX) with an intermediate of formula (X), wherein W is as defined above. Said reaction can be performed in a reaction-inert solvent such as, for example, N,N-dimethylformamide, and in the presence of a suitable base such as, for example, sodium hydride, preferably at a temperature ranging between room temperature and reflux temperature.

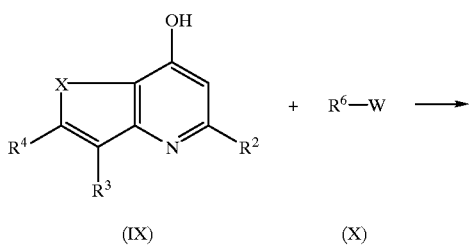

(IX)  (X)

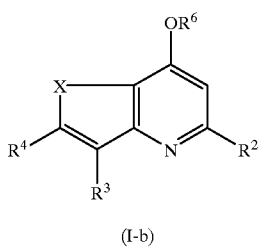

(I-b)

The compounds of formula (I) wherein $R^1$ is —$NHR^6$, represented by formula (I-c), can be prepared by N-alkylating an intermediate of formula (X) with an intermediate of formula $R^6$—W, wherein W is as previously defined. Compounds of formula (I-c) can be further N-alkylated with an intermediate of formula $R^5$—W, wherein W is as previously defined, yielding compounds of formula (I-d). These N-alkylations are conducted in a reaction-inert solvent such as, for example, an ether e.g. tetrahydofuran and preferably in the presence of a strong base, e.g. NaH.

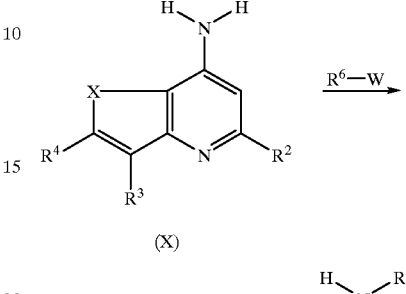

(X)

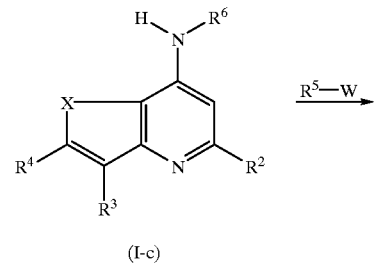

(I-c)

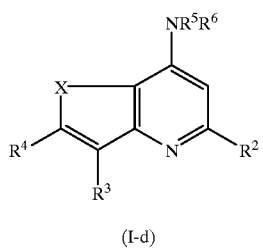

(I-d)

As outlined below, compounds of formula (I) may be converted into each other following art-known functional group transformation procedures.

For instance, compounds of formula (I) wherein X is S can be converted into compounds of formula (I) wherein X is $SO_2$ by an oxidation reaction, e.g. treatment with a peroxide such as 3-chloroperbenzoic acid in a reaction-inert solvent, e.g. dichloromethane.

Intermediates of formula (II) wherein X is S, said intermediates being represented by compounds of formula (II-a), can be prepared as outlined herebelow. Intermediates of formula (VI) are prepared by treating intermediates of formula (IV) with an ester of formula (V) in a reaction-inert solvent such as an alcohol, e.g. ethanol, preferably in the presence of a strong base such as, e.g. sodium ethoxide or sodium hydride. The intermediates (VI) are reacted with methanesulphonyl chloride and subsequently with ethyl thioglycolate in the presence of an excess of a suitable base such as, e.g. potassium bis(trimethylsilyl)amide, yielding aminothiophene derivatives of formula (VII). These are cyclized into intermediates (VIII) under acidic conditions and in the presence of an intermediate of formula $R^2$—C(OEt)=CH—COOEt. Intermediates of formula (VIII) are converted to intermediates (IX) using art-known hydrolysis methods, for example stirring in the presence of a base, and subsequent decarboxylation, e.g. by heating in a reaction-inert solvent such as e.g. diphenyl ether. Intermediates of formula (IX) are converted to intermediates of formula (II-a)

by treating intermediates (IX) with methanesulfonyloxy chloride or a halogenating reagent such as, e.g. POCl₃.

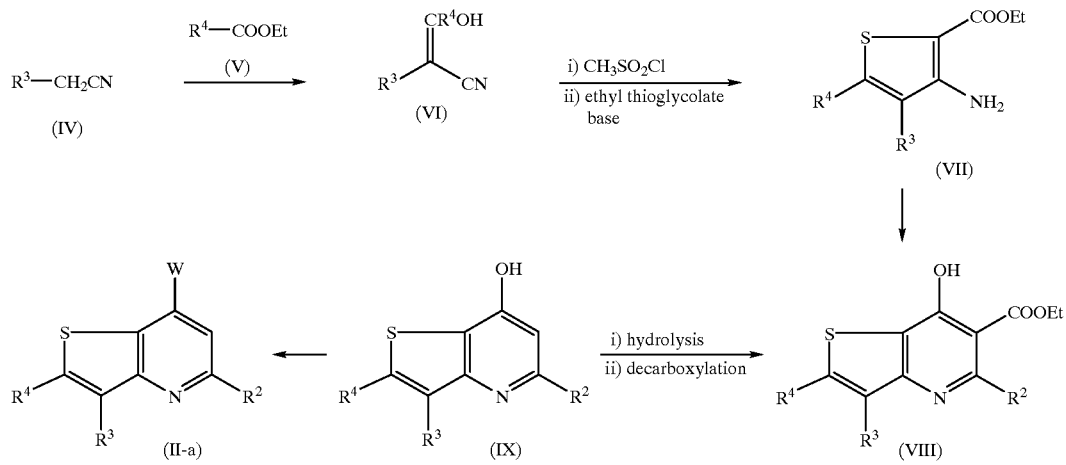

Intermediates of formula (X) are prepared by treating intermediates of formula (II) with ammonia.

Compounds of formula (I) and some of the intermediates may have one or more stereogenic centers in their structure, present in a R or a S configuration.

The compounds of formula (I) as prepared in the hereinabove described processes may be synthesized as a mixture of stereoisomeric forms, in particular in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The effectiveness of a compound as a CRF receptor antagonist may be determined by various assay methods. Suitable CRF antagonists of this invention are capable of inhibiting the specific binding of CRF to its receptor and antagonizing activities associated with CRF. A compound of structure (I) may be assessed for activity as a CRF antagonist by one or more generally accepted assays for this purpose, including (but not limited to) the assays disclosed by DeSouza et al. (*J. Neuroscience* 7:88, 1987) and Battaglia et al. (*Synapse* I:572, 1987). As mentioned above, suitable CRF antagonists include compounds which demonstrate CRF receptor affinity. CRE receptor affinity may be determined by binding studies that measure the ability of a compound to inhibit the binding of a radiolabeled CRF (e.g. [¹²⁵I]tyrosine CFR) to receptor (e.g., receptors prepared from rat cerebral cortex membranes). The radioligand binding assay described by DeSouza et al. (supra, 1987) provides an assay for determining a compound's affinity for the CRF receptor.

Such activity is typically calculated from the IC₅₀ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In addition to inhibiting CRF receptor binding, a compound's CRF receptor antagonist activity may be established by the ability of the compound to antagonize an activity associated with CRF. For example, CRF is known to stimulate various biochemical processes, including adenylate cyclase activity. Therefore, compounds may be evaluated as CRF antagonists by their ability to antagonize CRF-stimulated adenylate cyclase activity by, for example, measuring cAMP levels. The CRF-stimulated adenylate cyclase activity assay described by Battaglia et al. (supra, 1987) provides an assay for determining a compound's ability to antagonize CRF activity. Accordingly, CRF receptor antagonist activity may be determined by assay techniques which generally include an initial binding assay (such as disclosed by DeSouza (supra, 1987)) followed by a cAMP screening protocol (such as disclosed by Battaglia (supra, 1987)). With reference to CRF receptor binding affinities, CRF receptor antagonists of this invention have a $K_i$ of less than 10 μM. In a preferred embodiment of this invention, a CRF receptor antagonist has a $K_i$ of less than 1 μM, and more preferably less than 0.25 μM (i.e., 250 nM).

The CRF receptor antagonists of the present invention demonstrate activity at the CRF receptor site, and may be used as therapeutic agents for the treatment of a wide range of disorders or illnesses including endocrine, psychiatric, and neurologic disorders or illnesses. More specifically, the CRF receptor antagonists of the present invention may be useful in treating physiological conditions or disorders arising from the hypersecretion of CRF. Because CRF is believed to be a pivotal neurotransmitter that activates and coordinates the endocrine, behavioral and automatic responses to stress, the CRF receptor antagonists of the present invention can be used to treat neuropsychiatric disorders. Neuropsychiatric disorders which may be treatable by the CRF receptor antagonists of this invention include affective disorders such as depression; anxiety-related disorders such as generalized anxiety disorder, panic disorder, obsessive-compulsive disorder, abnormal aggression, cardiovascular abnormalities such as unstable angina and reactive hypertension; and feeding disorders such as anorexia nervosa, bulimia, and irritable bowel syndrome. CRF antagonists may also be useful in treating stress-induced immune suppression associated with various diseases states, as well as stroke. Other uses of the CRF antagonists of this invention include treatment of inflammatory conditions (such as rheumatoid arthritis, uveitis, asthma, inflammatory bowel disease and G.I. motility), Cushing's disease, infantile spasms, epilepsy and other seizures in both infants and adults, and various substance abuse and withdrawal (including alcoholism).

In another embodimnent of the invention, pharmaceutical compositions containing one or more CRF receptor antagonists are disclosed. For the purposes of administration, the compounds of the present invention may be formulated as pharmaceutical compositions. Pharmaceutical compositions of the present invention comprise a CRF receptor antagonist of the present invention (ie., a compound of structure (I)) and a pharmaceutically acceptable carrier and/or diluent. The CRF receptor antagonist is present in the composition in an amount which is effective to treat a particular disorder, that is, in an amount sufficient to achieve CRF receptor antagonist activity, and preferably with acceptable toxicity to the patient. Preferably, the pharmaceutical compositions of the present invention may include a CRF receptor antagonist in an amount from 0.1 mg to 250 mg per dosage depending upon the route of administration, and more preferably from 1 mg to 60 mg. Appropriate concentrations and dosages can be readily determined by one skilled in the art.

Pharmaceutically acceptable carrier and/or diluents are familiar to those skilled in the art. For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF receptor antagonist, diluents, dispersing and surface active agents, binders, and lubricants. One skilled in this art may further formulate the CRF receptor antagonist in an appropriate manner, and in accordance with accepted practices.

In another embodiment, the present invention provides a method for treating a variety of disorders or illnesses, including endocrine, psychiatric and neurologic disorders or illnesses. Such methods include administering of a compound of the present invention to a warm-blooded aniimal in an amount sufficient to treat the disorder or illness. Such methods include systemic administration of a CRF receptor antagonist of this invention, preferably in the form of a pharmaceutical composition. As used herein, systemic administration includes oral and parenteral methods of administration. For oral administration, suitable pharmaceutical compositions of CRF receptor antagonists include powders, granules, pills, tablets, and capsules as well as liquids, syrups, suspensions, and emulsions. These compositions may also include flavorings, preservatives, suspending, thickening and emulsifying agents, and other pharmaceutically acceptable additives. For parenetal administration, the compounds of the present invention can be prepared in aqueous injection solutions which may contain, in addition to the CRF receptor antagonist, buffers, antioxidants, bacteriostats, and other additives commonly employed in such solutions.

As mentioned above, administration of a compound of the present invention can be used to treat a wide variety of disorders or illnesses. In particular, the compounds of the present invention may be administered to a warm-blooded animal for the treatment of depression, anxiety disorder, panic disorder, obsessive-compulsive disorder, abnormal aggression, unstable angina, reactive hypertension, anorexia nervosa, bulimia, irritable bowel syndrome, stress-induced immune suppression, stroke, inflammation, Cushing's disease, infantile spasms, epilepsy, and substance abuse or withdrawal.

Hence, this invention provides the use of compounds of formula (I) for the manufacture of a medicine for treating physiological conditions or disorders arising from the hyper-secretion of corticotropin-releasing factor (CRF) and in particular for treating the disorders or illnesses mentioned above; and in a further embodiment the use of novel compounds of formula (I) as a medicine is provided.

The following examples are provided for purposes of illustration, not limitation.

EXPERIMENTAL PART

Hereinafter "THF" means tetrahydrofuran and "DCM" means dichloromethane.

A. Preparation of the Intermediates

Example A.1 a) A solution of 2,4,6-trimethylphenylacetonitrile (75 g) and ethyl formate (67 g) in 225 ml absolute ethanol was treated with solid sodium ethoxide (36 g) in small portions over 10 minutes, with good stirring. The mixture was heated to 60° C. under nitrogen for 16 hours, was allowed to cool to room temperature, and then poured into 1.2 l of water. This mixture was extracted with ether. The aqueous phase was acidified with 6M HCl to pH 1 and extracted with ethyl acetate. The ethyl acetate extracts were combined, washed with water and brine, dried and concentrated to give 46 g of 3-hydroxy-2-(2',4',6'-trimethylphenyl)acrylonitrile (intermediate 2). A sample was crystallized from ether/hexane to give colorless crystals, melting point=124–126° C.

b) A solution of intermediate (2) (1 g, 5.3 mmol) in 10 ml pyridine was cooled to 0° C. under nitrogen and then treated with methanesulfonyl chloride (0.67 g) with good stirring. The solution was stirred for 1 hour and then poured into water. This mixture was extracted with ethyl acetate. The organic phase was washed with 1M HCl, water and brine, dried and then concentrated to give 1.42 g of 3-methanesulfonoxy-2-(2',4',6'-trimethylphenyl) acrylonitrile (intermediate 3) as a brown solid. A sample was crystallized from ether/hexane to give colorless crystals, melting point=97–98° C.

c) A solution of intermediate (3) (1 g) in 40 ml of THF was treated with ethyl thioglycolate (0.45 g). This solution was treated with potassium bis(trimethylsilyl)amide (0.5M in toluene, 23 ml) via syringe. The reaction was allowed to stir overnight, and then poured into dilute aqueous HCl. The mixture was extracted with ethyl acetate, the organic phase was washed with 5% NaHCO$_3$, then brine, dried and concentrated. The crude mixture was crystallized from ether/hexane to give 1.0 g of 2-carboxy-3-amino-4-(2,4,6-trimethylphenyl)-thiophene, ethyl ester (intermediate 4).

d) A solution of intermediate (4) (1.5 g) and 75 mg p-toluenesulfonic acid monohydrate in 50 ml xylene and 3-ethoxy-ethylcrotonate (823 mg, 5.2 mmol) was stirred and heated to reflux under nitrogen. Solvent (25 ml) was removed by slow distillation over 1 hour. The solution was allowed to cool to room temperature and a solution of potassium tert-butoxide (570 mg) in 12 ml of absolute ethanol was added. This mixture was heated to 80° C. for 2 hours. This was allowed to cool to room temperature, treated with 0.6 ml acetic acid then concentrated to dryness. The residue was suspended in ethyl acetate stirred, filtered and washed to remove all the product from the potassium acetate. The filtrate was concentrated to a small volume and treated with diethyl ether to crystallize 1.7 g of 6-carboxyl-7-hydroxy-5-methyl-3-(2',4',6'-trimethylphenyl)thieno(3,2-b)pyridine, ethyl ester; (intermediate 5).

e) A solution of intermediate (5) (1.7 g) and 17.5 ml of 1M LiOH in 10 ml ethanol was stirred and heated to reflux under nitrogen for 16 hours. The solution was allowed to cool to room temperature then poured into a mixture of 15 ml of 1M hydrochloric acid in 100 ml of water. This was extracted with ethyl acetate, the organic phase washed with brine, dried and concentrated to give 6-carboxyl-7-hydroxy-5-methyl-3-(2',4',6'-trimethylphenyl)thieno(3,2-b)pyridine (intermediate 6). This was used directly in the next step.

f) A solution of intermediate (6) (400 mg) in 0.4 ml diphenyl ether was stirred and heated to 230° C. for 1.5 hour. The solution was allowed to cool to room temperature and 0.8 ml of $POCl_3$ was added. This mixture was heated to 100° C. for 2 hours, then allowed to cool to room temperature, and poured into 5% $NaHCO_3$. This was extracted with ethyl acetate, the organic phase washed with brine, dried and concentrated. The product was purified by flash chromatography ($SiO_2$) using 0 to 10% ether/hexane, to give 210 mg of 7-chloro-5-methyl-3-(2',4',6'-trimethylphenyl)thieno(3,2-b)pyridine (intermediate 1). $^1H$ NMR ($CDCl_3$): δ 2.02 (s, 6H), 2.36 (s, 3H), 2.59 (s, 3H), 5.25 (bs, 2H), 6.99 (s, 2H), 7.19 (s, 1H), 7.50 (s, 1H). Melting point=129–131° C.

Table 1 lists the intermediates that were prepared according to one of the above Examples.

TABLE I-1

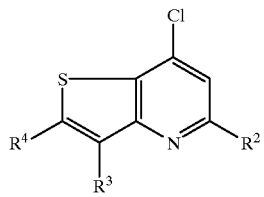

| Intm. No. | Ex. No. | $R^2$ | $R^4$ | $R^3$ |
|---|---|---|---|---|
| 1 | A.1 | $CH_3$ | H | 2,4,6-trimethylphenyl |

B. Preparation of the Final Compounds

Example B.1

A mixture of intermediate 1 (10 mg), p-toluenesulfonic acid (20 mg) and dipropylamine (50 μl) was stirred and heated to 195° C. for 1.5 hour. The solution was allowed to cool to room temperature, then dissolved in a mixture of water and ethyl acetate. This was extracted with ethyl acetate, the organic phase washed with brine, dried and concentrated. The product was purified by preparative TLC ($SiO_2$) using ethyl acetate/hexane, to give 7-(dipropylamino)-5-methyl-3-(2',4',6'-trimethylphenyl)thieno(3,2-b-pyridine) (compound 1).

Example B.2

Intermediate 1 (10 mg) in DMSO (0.2 ml) was treated with di-n-propylamine (0.1 ml) and tetraethylammonium iodide (9 mg) at 195° C. for 3.5 hours. The reaction was diluted with ethyl acetate and water and the organic layer was purified by silica gel preparative thin layer chromatography (ethyl acetate:hexane 2:3). Compound 6 was isolated and a small amount of compound 8 was also isolated.

Tables F-1 and F-2 list the compounds that were prepared according to one of the above Examples and table F-3 lists the analytical data for these compounds.

TABLE F-1

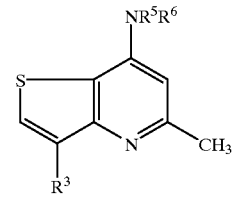

| Co. No. | Ex. No. | $R^5$ | $R^6$ | $R^3$ |
|---|---|---|---|---|
| 1 | B.1 | n-propyl | n-propyl | 2,4,6-trimethylphenyl |
| 2 | B.1 | ethyl | n-butyl | 2,4,6-trimethylphenyl |
| 3 | B.1 | n-propyl | cyclopropyl-methyl | 2,4,6-trimethylphenyl |
| 4 | B.1 | n-propyl | phenylmethyl | 2,4,6-trimethylphenyl |
| 5 | B.1 | 2-methoxyethyl | 2-methoxyethyl | 2,4,6-trimethylphenyl |
| 6 | B.1 | n-propyl | n-propyl | 2,4-dichlorophenyl |
| 7 | B.1 | 2-methoxyethyl | 2-methoxyethyl | 2,4-dichlorophenyl |

TABLE F-2

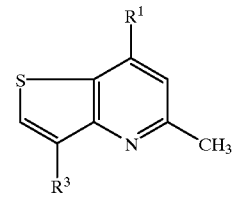

| Co. No. | Ex. No. | $R^1$ | $R^3$ |
|---|---|---|---|
| 8 | B.2 | $CH_3$—S— | 2,4,6-trimethylphenyl |

TABLE F-3

Analytical data

| Co. No. | Mass spectral data |
|---|---|
| 1 | 366 ($M^+$) |
| 2 | 366 ($M^+$) |
| 3 | 378 ($M^+$) |
| 4 | 414 ($M^+$) |
| 5 | 398 ($M^+$) |
| 6 | 392 ($M^+$) |
| 7 | 424 ($M^+$) |
| 8 | 313 ($M^+$) |

C. Pharmacological Examples

Example C.1: CRF Receptor Binding Activity

Compounds were evaluated for binding activity to the CRF receptor by a standard radioligand binding assay as generally described by DeSouza et al. (*J. Neurosci.* 7:88–100, 1987). By utilizing various radiolabeled CRF ligands, the assay may be used to evaluate the binding activity of the compounds of the present invention with any CRF receptor subtype. Briefly, the binding assay involves the displacement of a radiolabeled CRF ligand from the CRF receptor.

More specifically, the binding assay was performed in 1.5 ml Eppendorf tubes using approximately $1 \times 10^6$ cells per tube stably transfected with human CRF receptors. Each tube received about 0.1 ml of assay buffer (e.g., Dulbecco's phosphate buffered saline, 10 mM magnesium chloride, 20 $\mu$M bacitracin) with or without unlabeled sauvagine, urotensin I or CRF (final concentration, 1 $\mu$M) to determine nonspecific binding, 0.1 ml of [$^{125}$I] tyrosine-ovine CRF (final concentration~200 pM or approximately the $K_D$ as determined by Scatchard analysis) and 0.1 ml of a membrane suspension of cells containing the CRF receptor. The mixture was incubated for 2 hours at 22° C. followed by the separation of the bound and free radioligand by centrifugation. Following two washes of the pellets, the tubes were cut just above the pellet and monitored in a gamma counter for radioactivity at approximately 80% efficiency. All radioligand binding data was analyzed using a non-linear least-square curve-fitting program.

Binding activity corresponds to the concentration (nM) of the compound necessary to displace 50% of the radiolabeled ligand from the receptor. Compounds 1 to 8 have a $K_i \leq 250$ nM. Compounds 2 to 7 were found to show the best score in this test.

What is claimed is:

1. A compound of formula

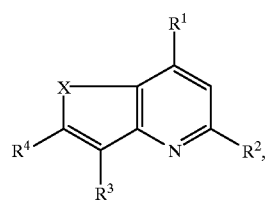

(I)

including the stereoisomers and the pharmaceutically acceptable acid addition salt forms thereof, wherein X is S or $SO_2$;

$R^1$ is $C_{1-6}$alkyl; $NR^5R^6$, $OR^6$ or $SR^6$;

$R^2$ is $C_{1-6}$alkyl, $C_{1-6}$alkyloxy or $C_{1-6}$alkylthio;

$R^3$ is $Ar^1$ or $Het^1$;

$R^4$ is hydrogen or $C_{1-6}$alkyl;

$R^5$ is hydrogen, $C_{1-8}$alkyl, mono- or di($C_{3-6}$cycloalkyl)methyl, $C_{3-6}$cycloalkyl, $C_{3-6}$alkenyl, hydroxy$C_{1-6}$alkyl, $C_{1-6}$alkylcarbonyloxy$C_{1-6}$alkyl or $C_{1-6}$alkyloxy$C_{1-6}$alkyl;

$R^6$ is $C_{1-8}$alkyl, mono- or di($C_{3-6}$cycloalkyl)methyl, $Ar^2CH_2$, $C_{1-6}$alkyloxy$C_{1-6}$alkyl, hydroxy$C_{1-6}$alkyl, $C_{3-6}$alkenyl, thienylmethyl, furanylmethyl, $C_{1-6}$alkylthio$C_{1-6}$alkyl, mono- or di($C_{1-6}$alkyl) amino$C_{1-6}$alkyl, di($C_{1-6}$alkyl)amino, $C_{1-6}$alkylcarbonyl$C_{1-6}$alkyl;

or $R^5$ and $R^6$ taken together with the nitrogen atom to which they are attached may form a pyrrolidinyl, piperidinyl, homopiperidinyl or morpholinyl group, optionally substituted with $C_{1-6}$alkyl or $C_{1-6}$alkyloxy$C_{1-6}$alkyl; and $Ar^1$ is phenyl; phenyl substituted with 1, 2 or 3 substituents each independently selected from halo, $C_{1-6}$alkyl, trifluoromethyl, hydroxy, cyano, $C_{1-6}$alkyloxy, benzyloxy, $C_{1-6}$alkylthio, nitro, amino and mono- or di($C_{1-6}$alkyl)amino;

$Het^1$ is pyridinyl; pyridinyl substituted with 1, 2 or 3 substituents each independently selected from halo, $C_{1-6}$alkyl, trifluoromethyl, hydroxy, cyano, $C_{1-6}$alkyloxy, benzyloxy, $C_{1-6}$alkylthio, nitro, amino, and mono- or di($C_{1-6}$alkyl)amino; and $Ar^2$ is phenyl; phenyl substituted with 1, 2 or 3 substituents each independently selected from halo, $C_{1-6}$alkyl, $C_{1-6}$alkyloxy, di($C_{1-6}$alkyl)amino$C_{1-6}$alkyl, or trifluoromethyl.

2. A compound according to claim 1 wherein $R^1$ is $NR^5R^6$ wherein $R^5$ is $C_{1-8}$alkyl or $C_{1-6}$alkyloxy$C_{1-6}$alkyl, and $R^6$ is $C_{1-8}$alkyl, $C_{1-6}$alkyloxy$C_{1-6}$alkyl, $Ar^2CH_2$ or $C_{3-6}$cycloalkylmethyl; $R^2$ is $C_{1-6}$alkyl; $R^3$ is a phenyl substituted with 1, 2 or 3 substituents each independently selected from $C_{1-6}$alkyl, $C_{1-6}$alkyloxy or halo, or $R^3$ is a pyridinyl substituted with 1, 2 or 3 substituents each independently selected from $C_{1-6}$alkyl or di($C_{1-6}$alkyl)amino; and $R^4$ is hydrogen or $C_{1-6}$alkyl.

3. A compound according to claim 1 wherein $R^1$ is $NR^5R^6$ wherein $R^5$ is $C_{2-4}$alkyl or $C_{1-2}$alkyloxy$C_{2-4}$alkyl and $R^6$ is $C_{2-4}$alkyl, $C_{1-2}$alkyloxy$C_{2-4}$alkyl, cyclopropylmethyl or phenylmethyl; $R^2$ is $C_{1-2}$alkyl; $R^3$ is phenyl substituted with 1, 2 or 3 substituents each independently selected from $C_{1-2}$alkyl, $C_{1-2}$alkyloxy or halo; $R^4$ is hydrogen or $C_{1-2}$alkyl.

4. A compound according to claim 1 wherein $R^1$ is $NR^5R^6$ wherein $R^5$ is $C_{2-4}$alkyl and $R^6$ is $C_{3-4}$alkyl, phenylmethyl, methoxyethyl or cyclopropylmethyl; $R^2$ is methyl; $R^3$ is 2,4,6-trimethylphenyl; and $R^4$ is hydrogen or methyl.

5. A compound according to claim 1 wherein the compound is 7-(dipropylamino)-5-methyl-3-(2',4',6'-trimethylphenyl)thieno(3,2-b)pyridine; or 7-(N-benzyl-N-propylamino)-5-methyl-3-(2',4',6'-trimethylphenyl)thieno (3,2-b)pyridine; a stereochemically isomeric form or a pharmaceutically acceptable acid addition salt thereof.

6. A composition comprising a pharmaceutically acceptable carrier, and as active ingredient a therapeutically effective amount of a compound as claimed in claim 1.

7. A process for preparing a composition wherein a therapeutically effective amount of a compound as claimed in claim 1 is intimately mixed with a pharmaceutically acceptable carrier.

8. A method of treating endocrine, psychiatric or neurologic disorder or illnesses in a warm-blooded animal comprising administering to the warm-blooded animal in need of treatment a therapeutically effective amount of the compound according to claim 1.

9. A compound of formula (II-a) wherein the radicals $R^2$, $R^3$ and $R^4$ are as defined in claim 1 and W is halo, mesyloxy or tosyloxy; a stereoisomeric form or an acid addition salt form thereof as follows:

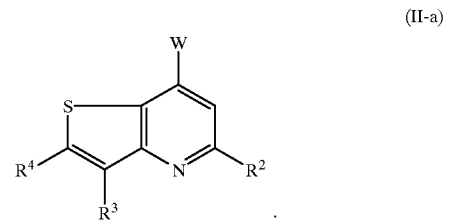

(II-a)

10. A process of preparing a compound of formula (I) as claimed in claim 1 wherein a) an intermediate of formula (II) is reacted with an intermediate of formula (III), wherein $R^{1'}$ has the meaning of $R^1$ other than $C_{1-6}$alkyl, thereby yielding compounds of formula (I-a);

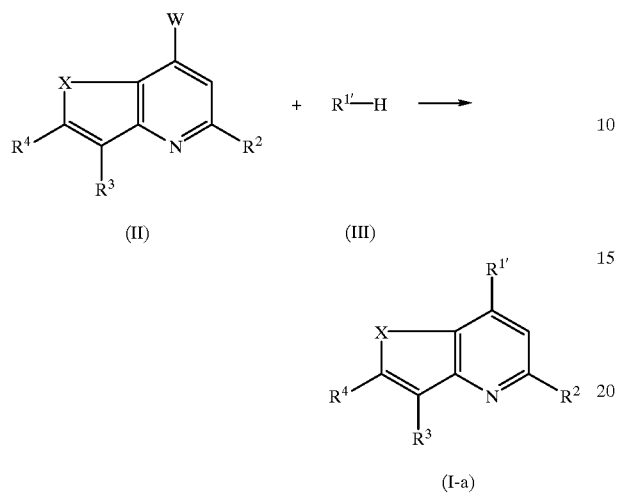

b) an intermediate of formula (IX) is O-alkylated with an intermediate of formula (X) in a reaction-inert solvent and in the presence of a suitable base, yielding compounds of formula (I-b), defined as compounds of formula (I) wherein $R^1$ is $OR^6$,

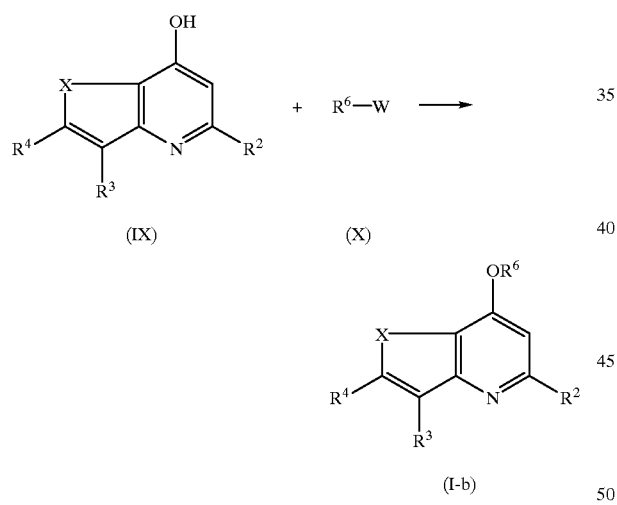

wherein in the above reaction schemes the radicals $R^1$, $R^2$, $R^3$, $R^6$ and X are as defined in claim 1 and W is an appropriate leaving group;

or, if desired, compounds of formula (I) are converted into each other following art-known tmsfonnation reactions; and further, if desired, compounds of formula (I) are converted into an acid addition salt by treatment with an acid, or conversely, the acid addition salt forms are converted into the free base by treatment with alkali; and, if desired, preparing stereochemically isomeric forms thereof.

11. A process of preparing a compound of formula (II-a) wherein a) an intermediate of formula (IX) is treated with methanesulfonyloxy chloride, benzenesulfonyloxy chloride or a halogenating reagent;

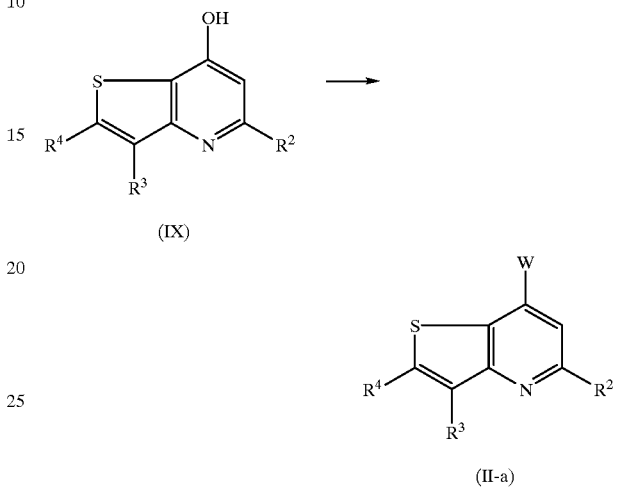

wherein in the above reaction scheme the radicals $R^2$, $R^3$ and $R^4$ are as defined in claim 1 and W is halo, mesyloxy or tosyloxy;

or, if desired, compounds of formula (II-a) are converted into each other following art-known transformation reactions; and further, if desired, compounds of formula (II-a) are converted into an acid addition salt by treatment with an acid, or conversely, the acid addition salt forms are converted into the free base by treatment with alkali; and, if desired, preparing stereochemically isomeric forms thereof.

12. A method of antagonizing a CRF receptor in a warm-blooded animal, comprising administering to the animal an effective amount of a compound of claim 1.

13. A method of treating a disorder manifesting hypersecretion of CRF in a warm-blooded animal, comprising administering to the animal an effective amount of a compound of claim 1.

14. The method of claim 13 wherein the disorder is selected from depression, an anxiety-related disorder, a feeding disorder, stress-induced immune suppression, stroke, Cushing's disease, infantile spasms, epilepsy, seizure, an inflammatory condition.

15. The method of claim 14 wherein the feeding disorder is anorexia nervosa, bulimia or irritable bowel syndrome.

16. The process according to claim 11 wherein the halogenating agent is $SOCl_2$ or $POCl_3$.

* * * * *